(12) United States Patent
Brewer

(10) Patent No.: US 9,733,169 B2
(45) Date of Patent: Aug. 15, 2017

(54) DISPERSIVE PIPETTE EXTRACTION TIP AND METHODS FOR USE

(71) Applicant: William E. Brewer, Columbia, SC (US)

(72) Inventor: William E. Brewer, Columbia, SC (US)

( * ) Notice: Subject to any disclaimer, the term of this patent is extended or adjusted under 35 U.S.C. 154(b) by 334 days.

(21) Appl. No.: 14/379,227

(22) PCT Filed: Feb. 14, 2013

(86) PCT No.: PCT/US2013/026217
§ 371 (c)(1),
(2) Date: Aug. 15, 2014

(87) PCT Pub. No.: WO2013/123253
PCT Pub. Date: Aug. 22, 2013

(65) Prior Publication Data
US 2015/0011016 A1  Jan. 8, 2015

Related U.S. Application Data

(60) Provisional application No. 61/599,057, filed on Feb. 15, 2012, provisional application No. 61/944,319, filed on Feb. 25, 2014.

(51) Int. Cl.
*G01N 1/40* (2006.01)
*B01L 3/02* (2006.01)

(52) U.S. Cl.
CPC ............ *G01N 1/405* (2013.01); *B01L 3/0275* (2013.01); *B01L 2200/0631* (2013.01); *B01L 2300/0681* (2013.01); *B01L 2400/086* (2013.01); *Y10T 436/255* (2015.01)

(58) Field of Classification Search
CPC ........... B01L 3/0275; B01L 2200/0631; B01L 2300/0681; B01L 2400/086; Y10T 436/25; G01N 1/405
See application file for complete search history.

(56) References Cited

U.S. PATENT DOCUMENTS

| | | | |
|---|---|---|---|
| 6,566,145 B2 | 5/2003 | Brewer | |
| 6,634,243 B1 | 10/2003 | Wickstead | |
| 6,770,246 B1 * | 8/2004 | Husek | B01L 3/0275 210/263 |
| 7,261,812 B1 * | 8/2007 | Karp | B01D 15/1864 210/198.2 |
| 7,448,287 B2 | 11/2008 | Daniel et al. | |
| 8,053,247 B2 | 11/2011 | Feuerstein et al. | |

(Continued)

OTHER PUBLICATIONS

Ahn, International Search Report and Written Opinion, Jun. 19, 2013, ISA/KR Aug. 22, 2013.

*Primary Examiner* — Erik B Crawford
*Assistant Examiner* — Gary E Hollinden
(74) *Attorney, Agent, or Firm* — Sara Centioni Kanos; Nexsen Pruet, LLC

(57) ABSTRACT

A pipette tip device for use in dispersive SPE. The device includes a pipette tip having a lower barrier, loose sorbent that is freely moveable during the extraction process, and a baffle system that is shaped to disrupt the flow of liquid sample that is aspirated into the pipette tip. The baffle system includes an insert that may be separate from or monolithic with the interior of the pipette tip.

24 Claims, 11 Drawing Sheets

(56) References Cited

U.S. PATENT DOCUMENTS

2010/0255484 A1* 10/2010 Halverson ............... G01N 1/38
435/6.1
2011/0079556 A1* 4/2011 Anderson-Smith .. B01D 63/087
210/633
2011/0107855 A1 5/2011 Motadel

* cited by examiner

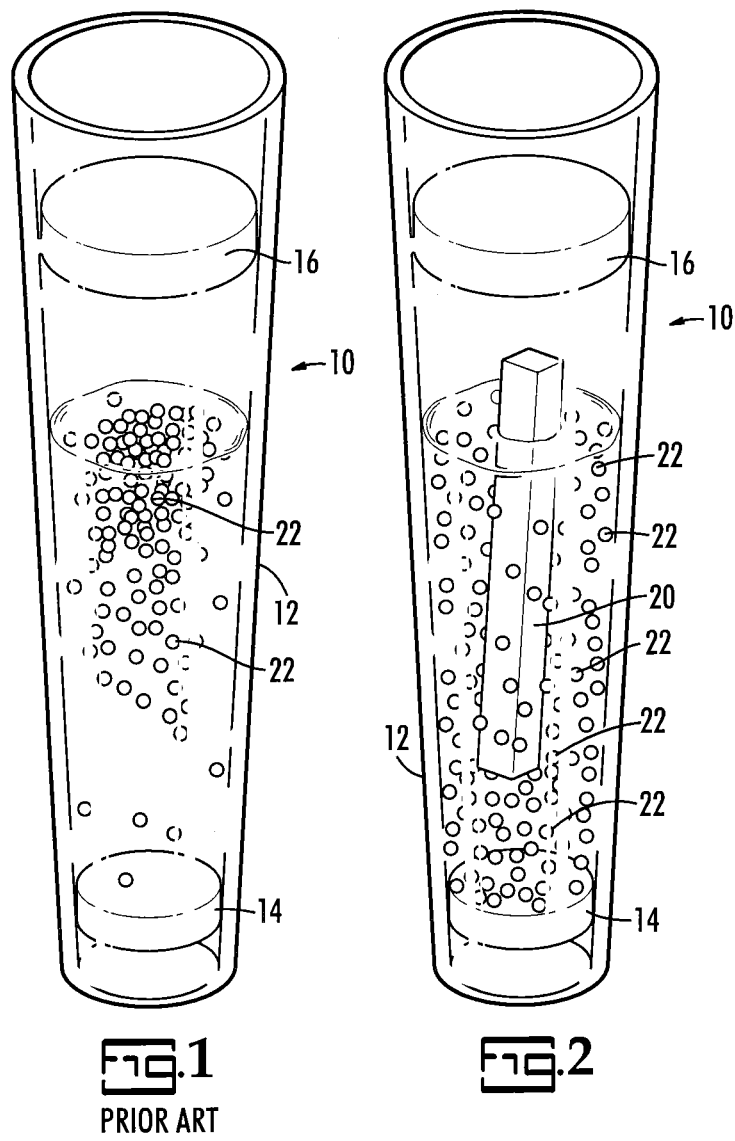

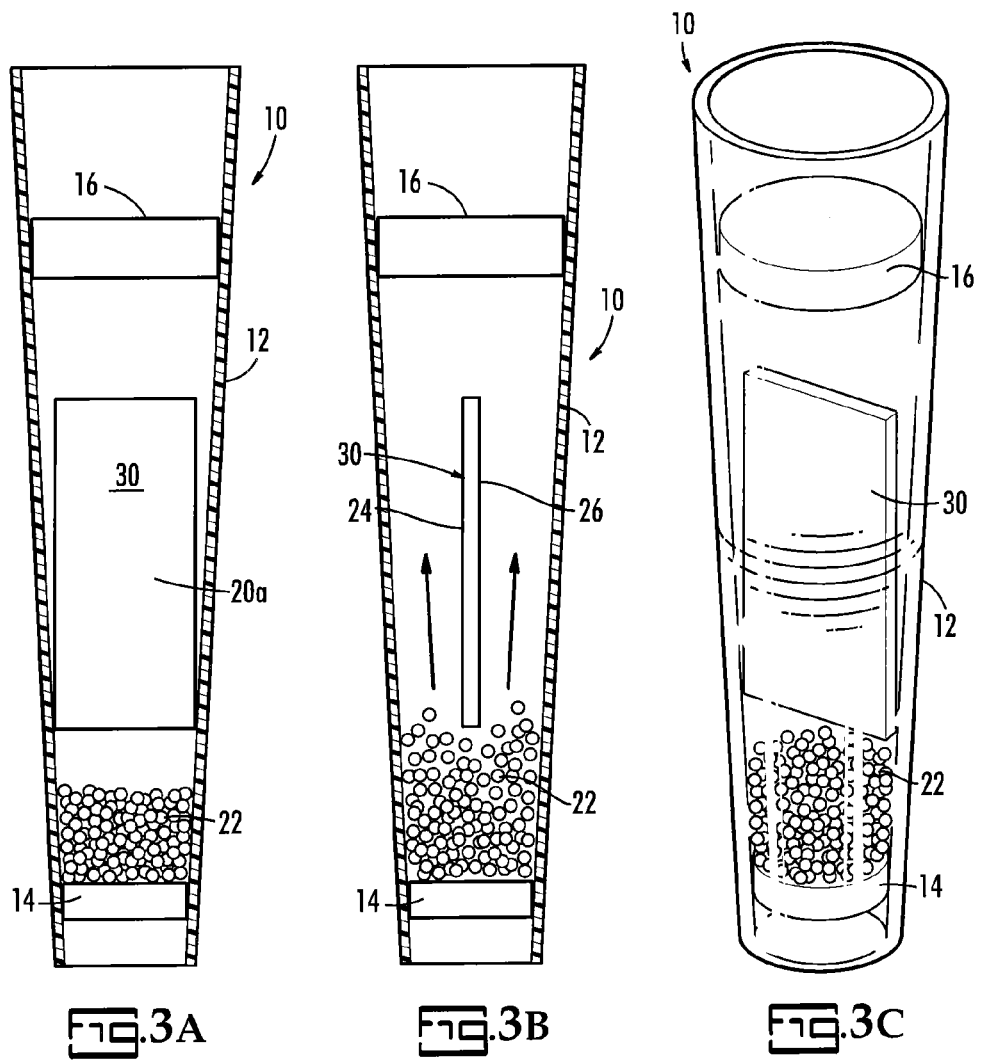

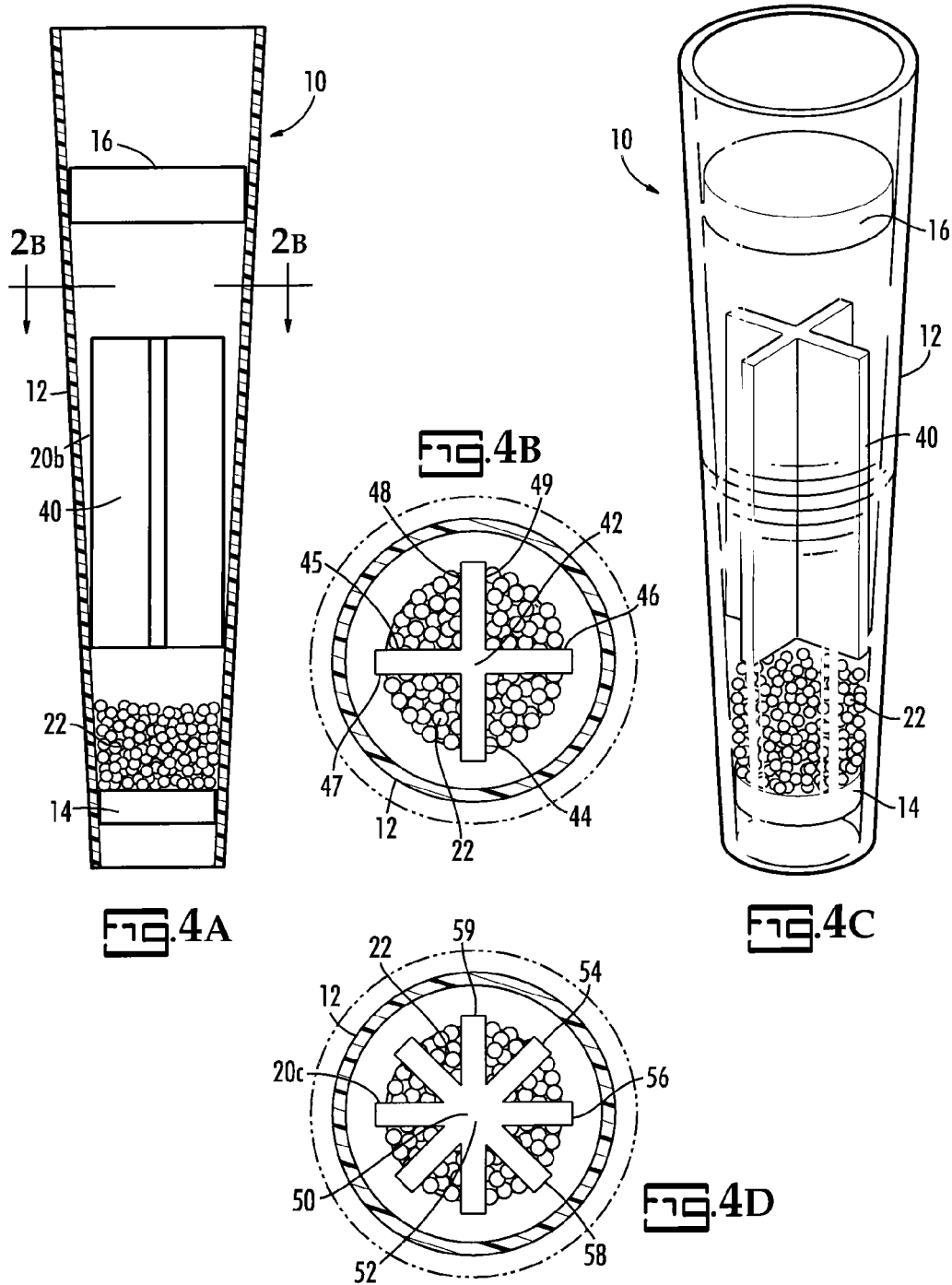

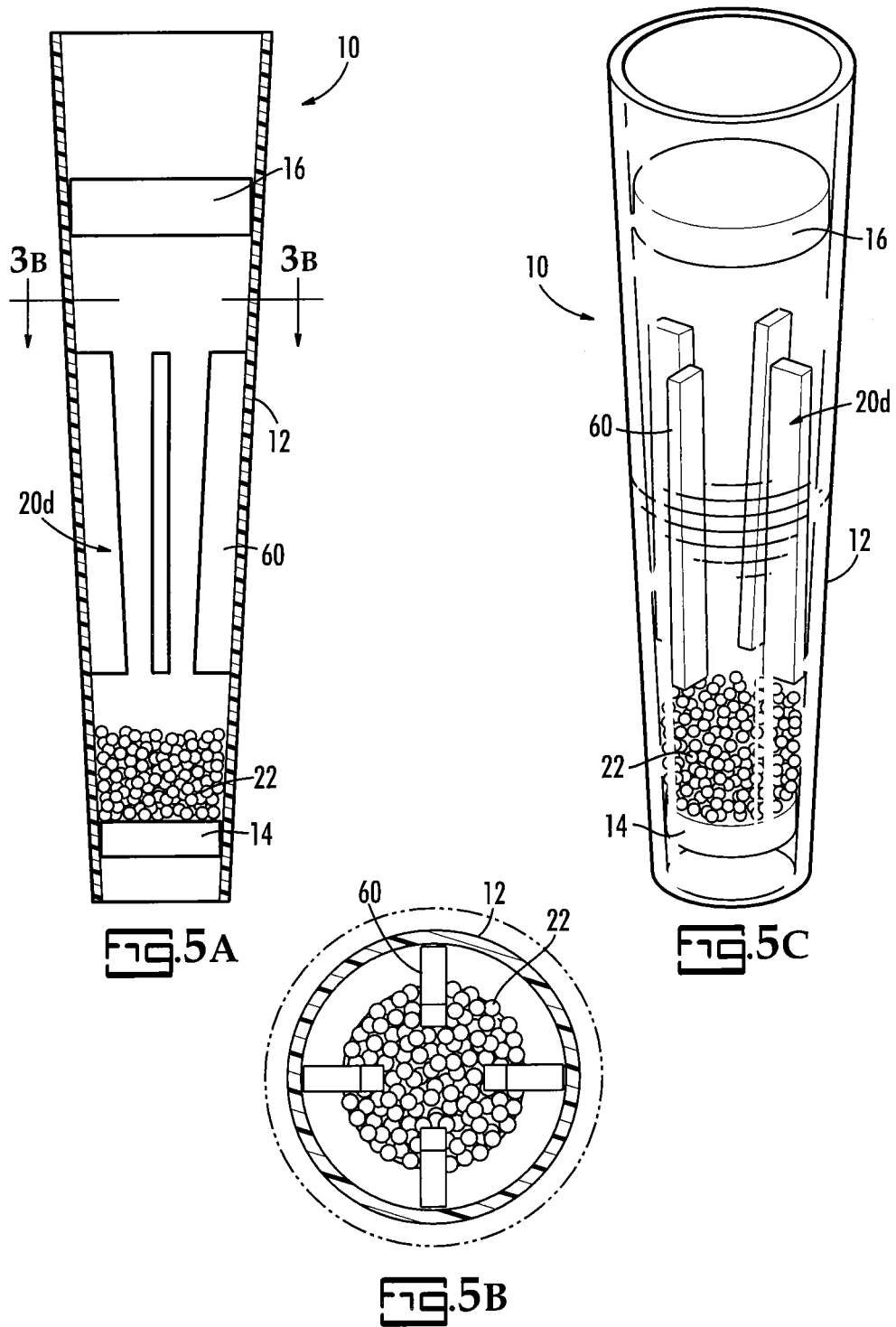

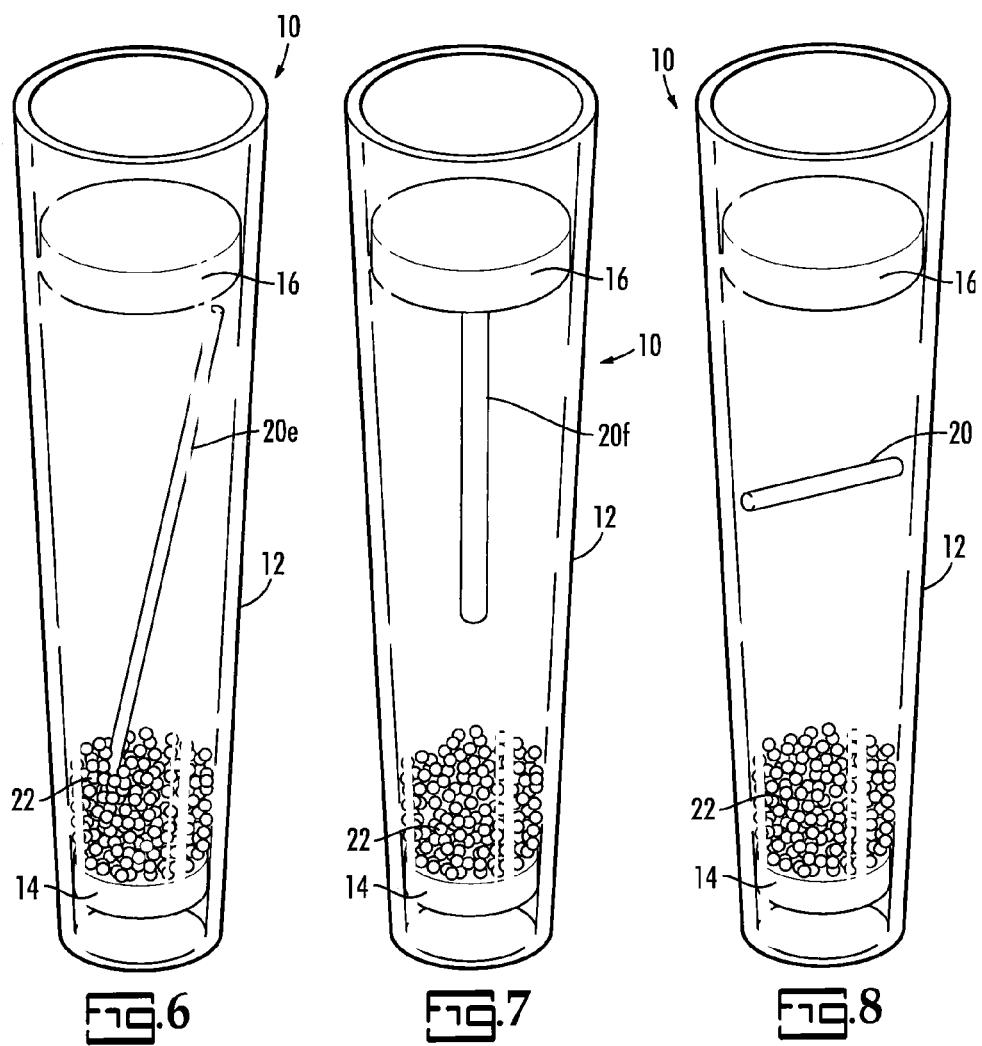

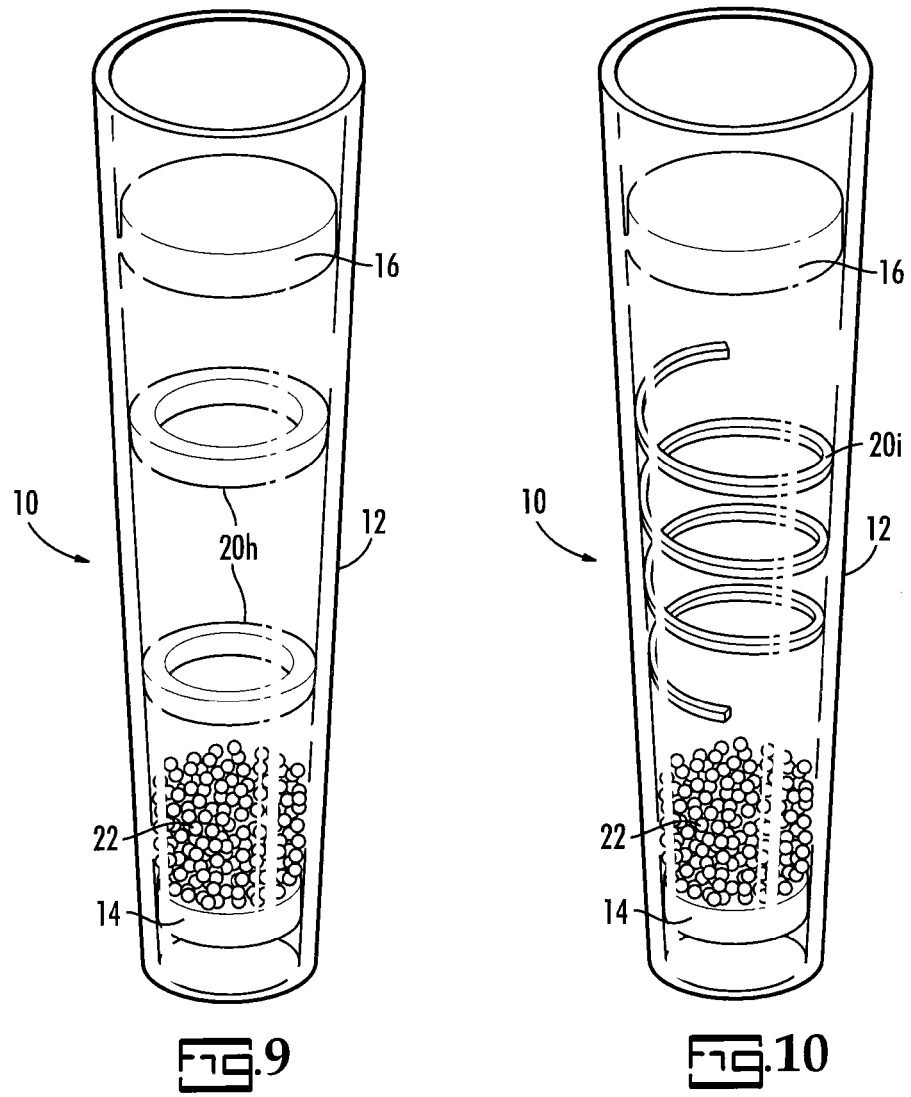

DISPERSIVE PIPETTE EXTRACTION TIP AND METHODS FOR USE

CROSS REFERENCE TO RELATED APPLICATIONS

The present application claims the benefit of priority of U.S. Provisional Application No. 61/599,057, filed on Feb. 15, 2012, which is incorporated herein in its entirety, PCT Application No. PCT/US2013/026217, filed Feb. 14, 2013, which is incorporated herein in its entirety, and U.S. Provisional Application No. 61/944,319, filed Feb. 25, 2014, which is incorporated herein in its entirety.

FIELD OF THE INVENTION

The present invention relates generally to an extraction device used during sample preparation for chemical analysis.

BACKGROUND OF THE INVENTION

Pipette tips for solid phase extraction (SPE) have been developed. Many of these use immobilized sorbent at the narrow end of the tip. The problems with these types of tips include solvent flow rates have to be controlled and the efficiency of the sorbent is not optimal because solution contact with the surface area of the sorbent is limited in fixed beds.

Some pipette extraction products, such as disposable pipette extraction products, including those described in U.S. Pat. No. 6,566,145, use loosely contained sorbent inside of the pipette tip. The sorbent is contained through the use of a screen or filter and an upper porous barrier. Being loosely contained, the sorbent is freely movable and is mixed with solutions providing unsurpassed efficiencies. Additionally, the extractions are rapid as compared to typical extraction methods because conditioning steps and slow flow rates are not required. This type of pipette tip extraction device utilizes dispersive SPE. As used herein, "dispersive" means: the solid phase sorbent may be thoroughly mixed with liquid solutions aspirated into the pipette tip.

While suitable for larger pipette tips, the disposable pipette extraction does not work well with narrow and low volume tips. For example, 5 mL and 1.3 mL disposable pipette extraction tips work well for extracting drugs from urine or pesticides from fruit and vegetable extracts. However, the disposable pipette extraction method is irreproducible when incorporated in 1 mL pipette tips that are used for 96 well plates and robotics. The poor reproducibility is mainly a result of inefficient mixing of the sorbent material with the sample solution. The sorbent bed after conditioning tends to adhere to the walls of the narrow tip, and consistent mixing with the sample solution is therefore difficult to achieve. Oftentimes, the sorbent bed floats on top of the sample solution rather than interacting with the solution, and irreproducibility occurs.

To overcome this problem, one device, known commercially by the name ASPIRE®, incorporates an intermediate porous barrier. The intermediate porous barrier ensures the sorbent is mixed with the solutions by aspirating and dispensing the solutions through the intermediate barrier. The intermediate barrier allows liquid solutions to pass through, but prevents the sorbent from passing through. However, a drawback to this type of extraction tip is that the intermediate barrier may cause losses in recovery because some of the liquid solution will inevitably get trapped by the porous membrane. Another drawback is that the existence of this barrier creates back pressure issues.

Accordingly, there exists a need for a dispersive SPE device that may be used to process liquid sample solutions for reproducible chemical analysis with low back pressure.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention; its sole purpose is to present concepts of the invention in a simplified form as a prelude to the more detailed description that is subsequently presented.

The present invention provides a pipette tip device for the extraction of liquid sample solutions. The device includes a pipette tip having a lower barrier, such as a frit, or screen at the narrow or lower end, and an upper barrier that is porous at the wide opening or upper end of the tip. Between these barriers is contained loose sorbent that is freely moveable during the extraction process.

Additionally, the device includes a baffle system interior to the pipette tip to facilitate dispersion and mixing by the development of turbulence as liquid is aspirated. Importantly, the baffle system causes the sorbent and the liquid sample to mix turbulently. The baffle system may comprise a dispersive insert, including a single piece presenting multiple faces to the fluid, each at an angle with respect to an adjacent surface or plural spaced-apart inserts with multiple, angled faces. The insert or inserts may be integral with or separate from the interior of the pipette tip. Furthermore, the insert or inserts may be movable or fixed within the pipette tip.

The flat surfaces parallel to fluid movement encourage mixing as a result of laminar flow; the angles at which adjacent surfaces are set produces mixing by turbulence. The baffle system may be located between the upper barrier and the lower barrier and may generally be parallel to or at an angle with the cylindrical axis of the pipette. The present baffle system also disrupts annular flow, but does not significantly retard axial flow as fluids are drawn in and expelled out. As used herein, the term "disrupt" means to introduce cross-flows, counter-flows or turbulence, and combinations thereof in flow rate of the fluid with respect to the sorbent in order to promote mixing time between aspiration and expulsion of the fluid from the pipette tip containing sorbent.

By way of example, the insert may be a single piece that is located between the upper and lower barriers, and above the sorbent bed. The insert is capable of disrupting or is shaped to disrupt the sorbent bed, and causing the sorbent to disperse into the liquid solution. As used herein, "shaped to disrupt" refers to a structure that is of sufficient size with respect to the pipette's internal dimensions to disrupt the fluid or sorbent movement during the aspiration of fluid into a pipette tip containing sorbent.

Normally, when liquid solutions are aspirated into the pipette extraction tip, the sorbent will tend to float and move upward into the tip and to the top of the liquid surface. Furthermore, the sorbent can form clumps. The insert disrupts this flow and prevents potential clumping. Not only does the insert act as a physical barrier that pushes and forces the sorbent to disperse and mix with the solution being aspirated, the insert disrupts the flow of the liquid sample by causing turbulence, which promotes the mixing between the sorbent and the liquid.

The insert may be a separate part that is introduced into the pipette tip device. Alternatively, the insert may be integral with or monolithic with the interior of the pipette tip. The insert may be nonporous or substantially nonporous so that the flow of liquid moves around the insert rather than through it. A smoother or flatter surface facilitates the liquid flow around the insert, which in turn creates additional turbulence to facilitate mixing. Should liquid flow through a porous insert, back pressure issues may result, as well as losses in recoveries.

There are various designs of inserts that may be utilized. One insert may be flat and rectangular or square in shape that is inserted into the pipette tip. Such insert provides two opposing faces for use in the dispersing of the sorbent through turbulent mixing with the liquid sample. As used herein, "turbulent mixing" refers to the combining of a liquid with a sorbent material in a tumultuous or disorderly manner.

Another example includes the use of a rod-like or wire-like, round insert that extends along the length of the pipette tip, about parallel to the cylindrical axis and into the narrow end of the tip. Alternatively, a wire-like insert could extend across the width, perpendicular to or at an angle with, the cylindrical axis of the pipette tip. In still another alternative, the rod-like insert could be connected to the upper barrier. These embodiments also facilitate turbulent mixing between the sorbent material and the liquid sample by disrupting the flow of the liquid and the sorbent movement.

Another insert may include a central stem having one or more ribs extending radially out from the cylindrical axis of the pipette tip, which provide multiple opposing faces for use in dispersing the sorbent. For example, the insert may include intersecting ribs, such as two rib members that perpendicularly intersect along the axis of the central stem to provide a cross-like shape from a top view. Alternatively, multiple intersecting ribs may be employed to provide additional shapes that form separate wedge-like spaces between the ribs. As with the prior embodiments, these provide sufficient disruption of the sorbent material by facilitating turbulent mixing.

Yet another insert may include one or more ridges or protrusions along the interior surface of the pipette tip. These ridges may be linear, and substantially parallel to or at an angle with the cylindrical axis of the pipette tip, and may extend radially toward the cylindrical axis of the pipette tip. Alternatively, these ridges may be curved, or spiral-like in design, and may extend radially, longitudinally and azimuthally with respect to the cylindrical axis of the pipette tip. Again, these embodiments provide for turbulent mixing between the sorbent material and the liquid sample.

Another feature of the insert is that it may be formed to serve a mechanical and/or chemical function during the extraction or chemical analysis. For example, the insert may have a surface with reactive properties or agents that may affect either the extraction of the analyte or the sample matrix, or have the ability to perform an immunoassay screen or measure pH. If only serving a mechanical function, the surface of the insert or inserts may be flat, nonporous and inert. Thus, the pipette tip device of the present invention could be used not only to extract drugs from a sample, such as a urine sample, but it could also be employed to simultaneously perform an immunoassay drug screen or test for adulterants.

The present invention can also include a method. In one embodiment, a method for filtering solutions includes the following steps: 1) providing a dispersive pipette tip, as described herein; 2) aspirating serum into the tip; 3) aspirating solvent into the tip; 4) mixing within the tip with air; 5) dispensing clean solution; and, optionally, 6) repeating the aspiration and dispensing of solution 1 to 2 times. One feature of this method is that the sorbent in the tips preferably binds matrices of the serum, which cause ion suppression and interference in LC/MS analysis. The solvent helps to "crash the proteins", and the combination of sorbent and the frit help to filter the solution. All of this is can be accomplished in about 30 seconds without the need for centrifugation or filtration.

Other features and their advantages will be readily apparent to those skilled in chemical arts from a careful reading of the Detailed Description of Preferred Embodiments, accompanied by the following drawings.

BRIEF DESCRIPTION OF THE DRAWINGS

FIG. 1 includes a perspective view of a prior pipette tip device having no baffle system;

FIG. 2 includes a perspective view of a pipette tip device having a baffle system according to an embodiment of the present invention;

FIG. 3A includes a cross sectional view of a pipette tip device showing the front of a baffle system according to an embodiment of the present invention;

FIG. 3B includes a cross sectional view of a pipette tip device showing the side of a baffle system according to an embodiment of the present invention;

FIG. 3C includes a perspective view of a pipette tip device according to an embodiment of the present invention;

FIG. 4A includes a cross sectional view of a pipette tip device showing the front of a baffle system according to an alternative embodiment of the present invention;

FIG. 4B includes a cross sectional view of a pipette tip device at cross section line 2B according to an alternative embodiment of the present invention;

FIG. 4C includes a perspective view of a pipette tip device according to an alternative embodiment of the present invention;

FIG. 4D includes a cross sectional view of a pipette tip device showing the top of a baffle system according to an alternative embodiment of the present invention;

FIG. 5A is a cross sectional view of a pipette tip device according to an alternative embodiment of the present invention;

FIG. 5B is a cross sectional view of a pipette tip device at cross section line 3B according to an alternative embodiment of the present invention; and FIG. 5C is a perspective view of a pipette tip device according to an alternative embodiment of the present invention.

FIG. 6 is a perspective view of a pipette tip device according to an alternative embodiment of the present invention;

FIG. 7 is a perspective view of a pipette tip device according to an alternative embodiment of the present invention;

FIG. 8 is a perspective view of a pipette tip device according to an alternative embodiment of the present invention;

FIG. 9 is a perspective view of a pipette tip device according to an alternative embodiment of the present invention;

FIG. 10 is a perspective view of a pipette tip device according to an alternative embodiment of the present invention;

DETAILED DESCRIPTION

Figures 11A, 11B:
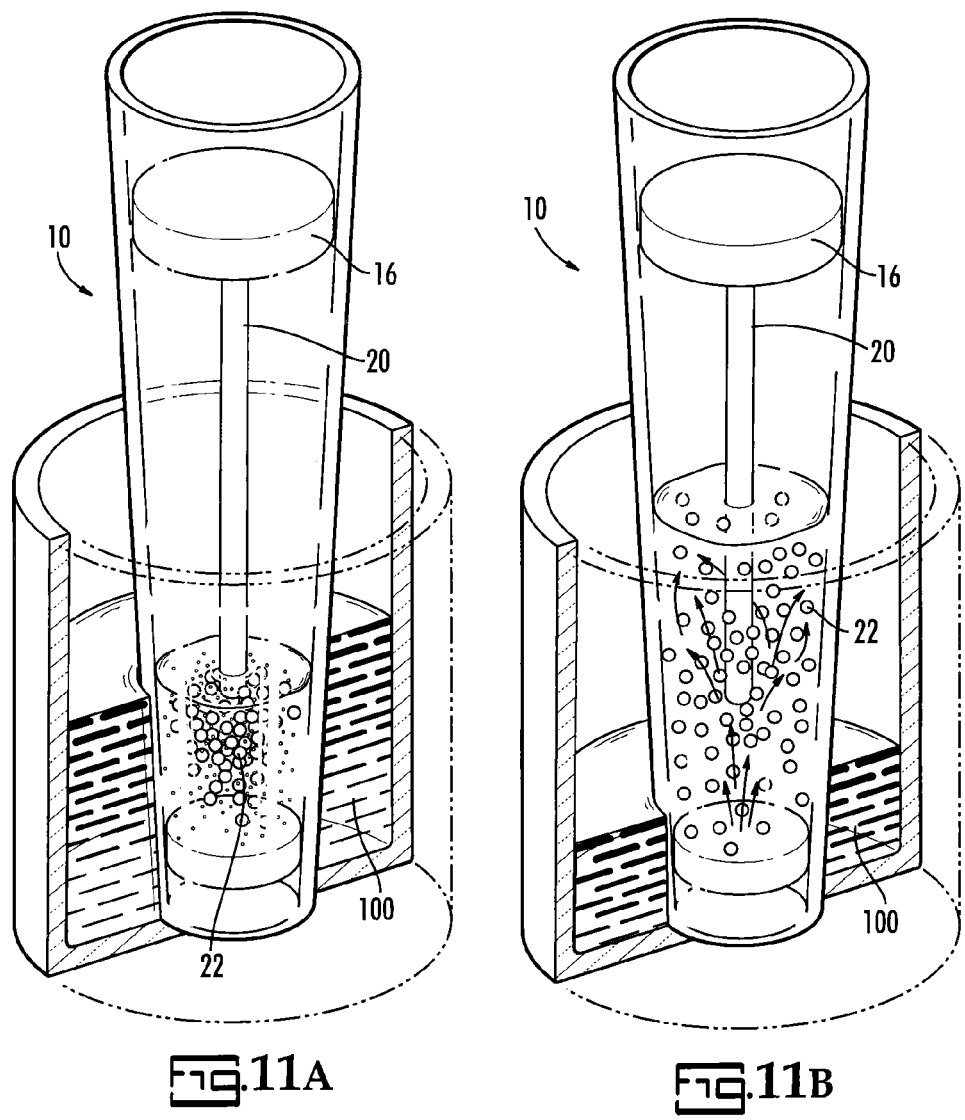
FIG. 11A is a perspective view of a pipette tip device being used in an extraction step according to a method of the present invention.
FIG. 11B is a perspective view of a pipette tip device being used in an extraction step according to a method of the present invention.

The present invention provides a pipette tip device 10 and method for the extraction of liquid sample solutions. The device includes a pipette tip 12 having a lower barrier 14, such as a frit, or screen a closure with a slit, or a closure with multiple slits, at the narrow or lower end, and an upper barrier 16 that is porous at the wide opening or upper end of the tip. Between these barriers is contained loose sorbent 22 that is freely moveable during the extraction process.

Additionally, the device 10 includes a baffle system 20 interior to the pipette tip 12 to facilitate dispersion and mixing between the sorbent 22 and the liquid sample by the development of turbulence when the pipette tip 12 is aspirated with liquid. The use of the baffle system 20 promotes enhanced and consistent results when performing solid phase extractions.

As shown in FIG. 1, prior pipette tip devices that do not include a baffle system 20 tend to result in clumping of the sorbent 22 and ultimately in mixtures that are varied and inhomogenous. Thus, the extractions are not entirely effective or reproducible. With the inclusion of a baffle system 20, such as shown in FIG. 2, however, a homogenous or uniform mixture results when the sorbent 22 and the liquid sample are combined.

The shape and dimension of the baffle system 20 can vary provided that it facilitates or creates turbulent mixing between the sorbent material 22 and a liquid sample. Particularly, the baffle system 20 functions to disrupt the flow of the liquid sample and sorbent movement through the pipette tip 12 by causing turbulence and mixing.

The surface of the baffle system 20 may be flat or smooth, nonporous, or substantially nonporous and inert. Alternatively, the surface may include reactive properties. For example, the baffle system 20 may have a surface with reactive properties or agents that may affect either the extraction of the analyte or the sample matrix, or have the ability to perform an immunoassay screen or measure pH.

In one embodiment, shown in FIGS. 3A-3C, the baffle system 20a is between the upper and lower barriers, 16, 14, respectively, and above the sorbent 22. In this embodiment, the baffle system 20a includes a single insert 30 that is generally flat and rectangular in shape with a first face 24 opposing a second face 26.

In this embodiment, the insert 30 is dimensioned to be inserted into the wide, upper end of the pipette tip 12. Particularly, the shape of the insert is such that the base 32 of the insert 30 becomes lodged or abuts the interior walls of the narrow, lower end of the pipette tip 12 at either side of the lower end of the insert 30. As shown, the insert 30 may be placed upright so that it is about parallel to the cylindrical axis of the pipette tip 12. Alternatively, the insert 30 may be placed at a lean and at an angle with the cylindrical axis of the pipette tip 12. Moreover, the insert 30 may be moveable or fixed within the pipette tip 12 when liquid sample is introduced.

As shown in FIG. 1b, baffle system 20a serves to disrupt liquid flow by forcing the liquid and sorbent to move around the insert 30, and thereby enhance the uniform mixing of the sorbent material 22 as liquid is aspirated into the pipette tip 12. Generally, the properties of the baffle system 20a are such that turbulent mixing between the liquid sample and the sorbent material 22 is facilitated, and sorbent clumping or non-uniform mixing is avoided.

Particularly, the bottom of the insert 30 provides a physical barrier to the upward movement of the sorbent and liquid. Based on the shape and location of the insert, the sorbent and liquid must move around it and flow next to the opposing faces 24 and 26. By forcing the sorbent and liquid to move to either side of the insert 30, additional turbulence is created. Furthermore, the opposing faces 24 and 26 may be at an angle with respect to the adjacent walls of the pipette tip 12, which further disrupts the flow of the liquid and movement of the sorbent 22.

An alternative embodiment of the baffle system is shown in FIGS. 4A-4C. Particularly, the baffle system 20b includes an insert 40 with a stem 42 that is an axially-extending construction between the upper and lower barriers 16 and 14. The stem 42 is formed by two axially-extending rib members, 44 and 46. The rib members 44 and 46 perpendicularly intersect along the axis of the stem 42. Further, the rib members each provide multiple, opposing faces, 45, 47 and 48, 49.

As shown, the insert 40 may be placed upright within the pipette tip 12 so that the rib members 44 and 46, extend out radially from the axis of the stem 42, which is about co-axial with the cylindrical axis of the pipette tip 12. Alternatively, the insert 40 may be placed at an angle other than about zero with respect to the cylindrical axis of the pipette tip 12.

As with the prior embodiment, the insert 40 of baffle system 20b is shaped to disrupt the sorbent material 22 and a liquid sample. In use, the baffle system 20b forces the flow of the liquid sample and sorbent 22 around the insert 40, which creates turbulence for enhanced mixing between the sorbent and the liquid.

It is therefore contemplated by the present invention that the baffle system 20 may include a variety of shapes and dimensions to disrupt sorbent 22 and liquid samples. For example, the baffle system 20c, shown in FIG. 4D is similar to the baffle system 20b except that additional rib members are included. In particular, the baffle system 20c includes an insert 50 having a stem 52 formed by four intersecting rib members 54, 56, 58 and 59. The ribs are shown as evenly spaced apart. Alternatively, the ribs may be unevenly spaced. Other baffle systems of this type may include one or more ribs that extend out from a stem.

Another alternative embodiment is shown in FIGS. 5A-5C. In this embodiment, the baffle system 20d includes one or more ridges 60 or protrusions that extend out from the interior surface of the pipette tip 12. As illustrated, each ridge 60 may be linear in shape and extend vertically along the length of the pipette tip 12 from the upper end to the lower end of the tip 12, and between the upper and lower barriers, 16 and 14. Particularly, the ridges 60 may be spaced apart evenly. Alternatively, the ridges 60 are spaced apart at uneven intervals. Importantly, the ridges 60 disrupt the liquid sample by promoting turbulent mixing and by creating additional turbulence in the flow of the liquid sample and the movement of the sorbent 22.

In yet another alternative embodiment, wire-like or rod-like baffle systems that are rounded in shape are used. In one example, shown in FIG. 6, a rod-like baffle system 20e is shown between the upper and lower barriers 16 and 14, and placed at a lean with respect to the cylindrical axis of the pipette tip 12. Alternatively, in FIG. 7, a rod-like baffle system 20f is shown as being connected with the upper barrier 16 and extending vertically down into the pipette tip 12. Still another example, shown in FIG. 5, includes a rod-like baffle system 20f that extends horizontally across the interior of the pipette tip 12.

Even other alternative embodiments are shown in FIGS. 9-10. The baffle system 20h in FIG. 9 includes ridges along the interior of the pipette tip 12 that may extend horizontally between the upper and lower barriers, 16 and 14. Such ridges may be annular in shape. Alternatively, the baffle system 20i includes ridges along the interior of the pipette tip 12 that may have a spiral shape and that may run clockwise or counter-clockwise, as shown in FIG. 10.

Among the alternative types of baffle systems, each includes surfaces that participate in the disruption of the sorbent 22 during the extraction process. Such surfaces may have a variety of properties. In some instances, the surfaces of the baffle system may be flat or smooth, inert and nonporous. In other instances, the surfaces of the baffle system may be rounded or generally not uniform. Furthermore, reactive properties may be included on the surfaces. Moreover, among the alternative types, each of the baffle system may either be separate from or integral and monolithic with the pipette tip. Thus, each baffle system is shaped to disrupt to the liquid sample by promoting turbulent mixing between the sorbent 22 and the liquid sample.

Figure 11C:
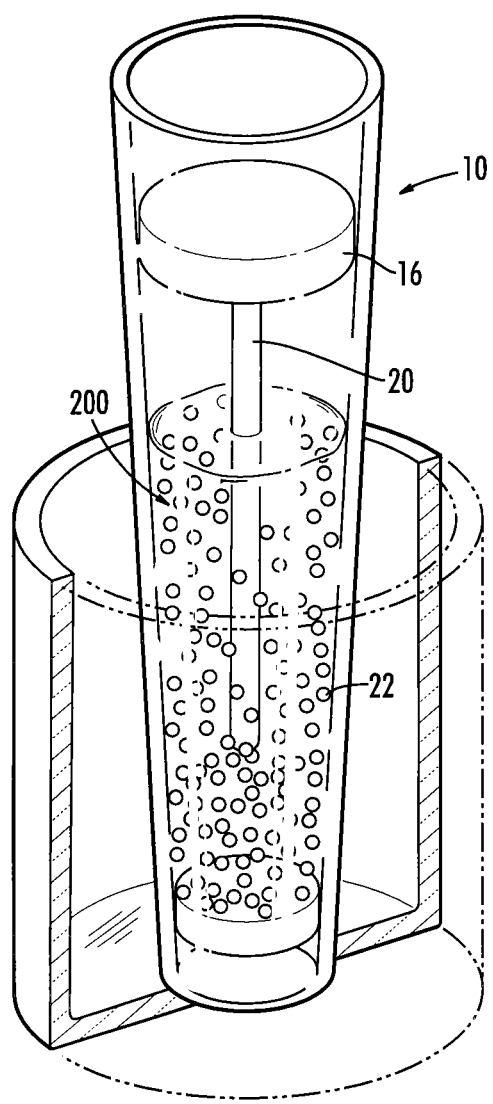
FIG. 11C is a perspective view of a pipette tip device being used in an extraction step according to a method of the present invention.

The present invention further contemplates a method of dispersive SPE through the use of the pipette tip device 10. In one embodiment of the method of the present invention, various steps are shown in FIGS. 11A-11C. Particularly, the method may include the following steps: 1) providing a dispersive SPE pipette tip device 10, wherein the pipette tip includes a baffle system 20 as described above; 2) providing a sample solution 100; 3) aspirating the sample solution 100 into the pipette tip device 10; and 4) combining the sorbent 22 with the sample 100 in the presence of the baffle system 20 to form a uniform mixture 200 and to perform the SPE extraction. Additionally, the method may include the steps of collecting the extracts, or, alternatively, dispensing the resulting solution to waste, and then repeating the steps 3) and 4) with wash and elution solvent.

As illustrated in FIG. 11A, when the liquid sample 100 is first drawn into the pipette tip device 10, the sorbent submerges and absorbs the liquid. The baffle system 20, in FIG. 11B next disrupts the liquid sample 100 as it continues to be aspirated into the pipette tip. In turn, the disruption creates a uniform mixture 200 of the sorbent 22 and the liquid 100, as shown in FIG. 11C. This method and device, therefore, enhances the effectiveness and reproducibility of SPE extractions.

The present invention can also include another method. In one embodiment, a method for removing proteins and matrix interferences from serum, plasma or whole blood includes the following steps: 1) providing a dispersive pipette tip, as described herein; 2) aspirating serum or plasma or whole blood into the tip; 3) aspirating solvent into the tip; 4) mixing within the tip with air; 5) dispensing clean solution; and, optionally, 6) repeating the aspiration and dispensing of solution 1 to 2 times. One feature of this method is that the sorbent in the tips preferably binds matrices of the blood, which cause ion suppression and interference in LC/MS analysis. The solvent helps to "crash the proteins", and the combination of sorbent and the frit help to filter the solution. All of this is can be accomplished in about 30 seconds without the need for centrifugation or filtration. Furthermore, reagents that cause protein precipitation of blood, such as trichloroacetic acid or zinc sulfate, can be added to the sorbent in the DPX tip to enhance protein removal. The bottom frit and sorbent are used to filter the protein precipitate, which removes the solid particulate material from the resulting sample solution.

The following examples are intended to illustrate, and not limit, the invention disclosed herein.

EXAMPLES

Example 1

A drug mixture of opiates is extracted from urine using the dispersive SPE pipette tip device 10. The first series of extractions (a) use pipette tips without a baffle system, and the second series (b) of extractions use pipette tips with a baffle system. The final extracts were analyzed by liquid chromatography with tandem mass spectrometry (LC/MS/MS). The results of 8 replicates of the pipette tips without baffle systems show relative peak intensities with 15.6% relative standard deviation (RSD). However, with the baffle system in place, the % RSD is less than 5%. In fact, the % RSD of the peak intensities with the baffle system are relatively identical to the % RSD of the peak intensities of a neat (unextracted) standard of opiates injected repeatedly into the LC/MS instrument.

Example 2

Figure 12:
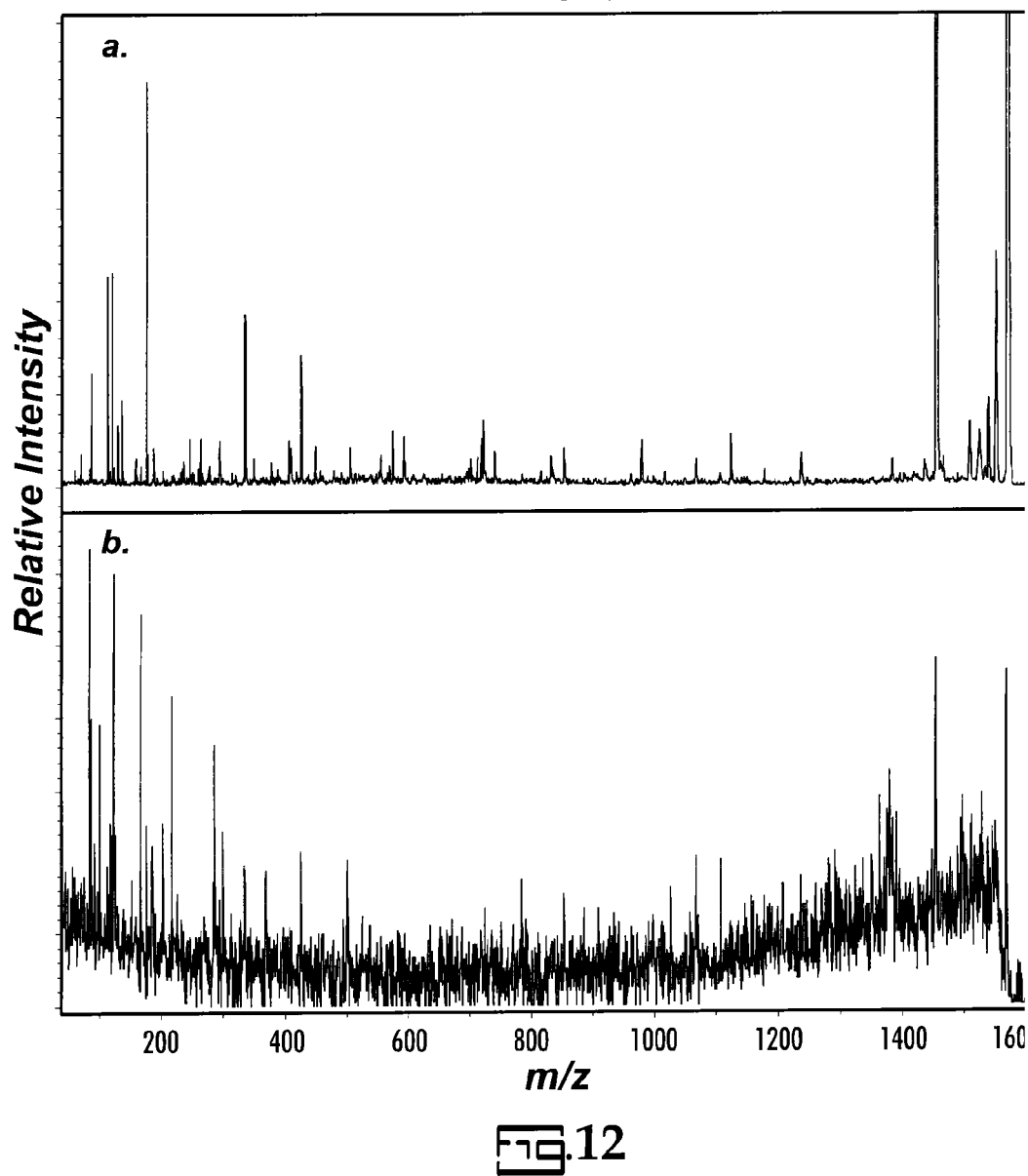
FIG. 12 is a chromatogram comparing dispersive pipette tip technology to fixed resin pipette tip technology according to an embodiment of the present invention.

As shown in FIG. 12, a MALDI-TOF MS of trypsin digested bovine serum albumin (BSA) (1 µg) after reverse phase extraction with two different micropipette tips. The results for (a.) were taken after a dispersive pipette tip device 10 of the present invention was aspirated two times with a liquid sample. The results for (b.) were taken after a fixed resin reverse phase pipette tip was aspirated ten times with a liquid sample. Comparing (a.) including the use of pipette tip device 10 of the present invention (dispersive technology) to (b.) including the use of fixed resin reverse phase pipette tips, the results show higher signal intensities with greater sequence coverage for samples recovered using dispersive pipette tips 10. The relative intensity for (a.) has been normalized to (b.) for comparison purpose.

Example 3

Figure 13:
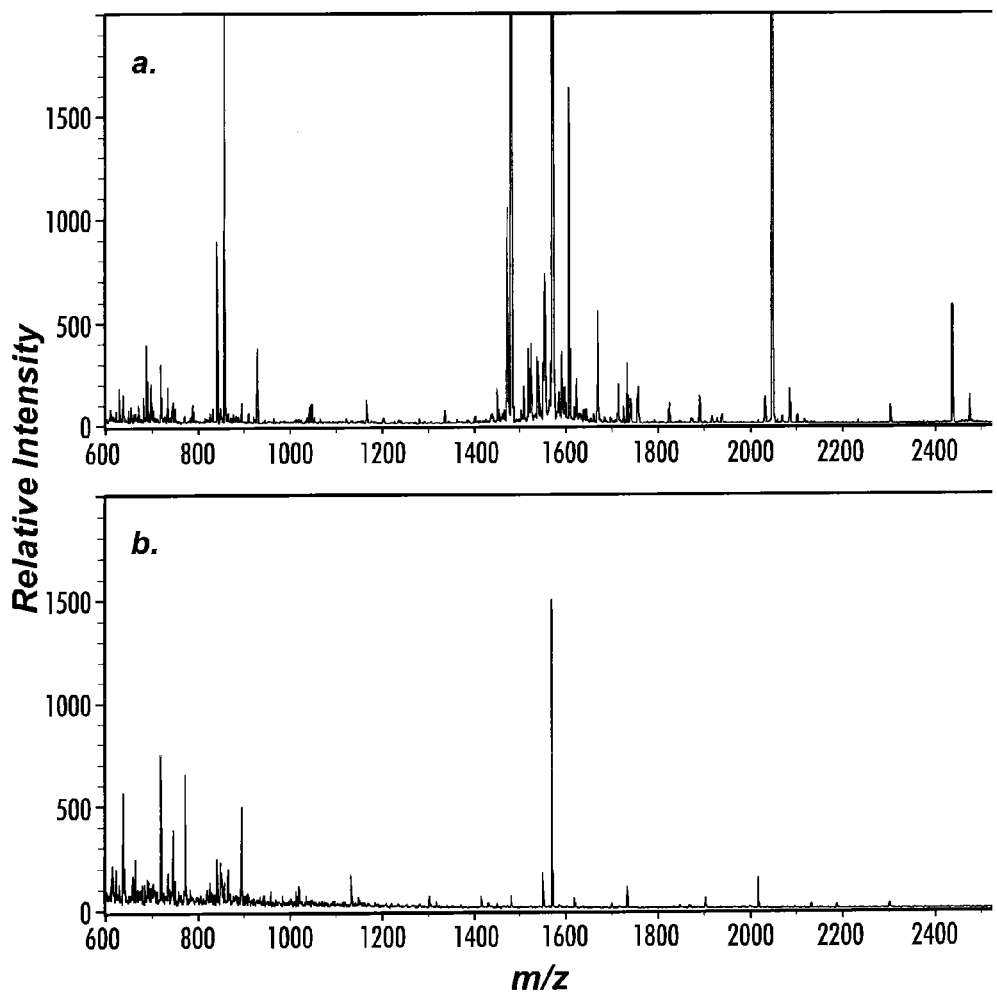
FIG. 13 is a chromatogram comparing dispersive technology to fixed resin pipette tip technology according to an embodiment of the present invention.

As shown in FIG. 13, tandem mass spectrometry of a peptide (m/z 1568) obtained on MALDI-TOF/TOF. The results for (a.) were taken after a dispersive pipette tip device 10 of the present invention was aspirated two times with a liquid sample. The results for (b.) were taken after a fixed resin reverse phase pipette tip was aspirated ten times with a liquid sample. Comparing (a.) dispersive technology to (b.) fixed resin reverse phase pipette tips, the peptide fragmentation signals have higher signal to noise ratios with full coverage of all y and b ions for (a.). The two spectra are not to scale with respect to each plot.

Example 4

Figure 14:
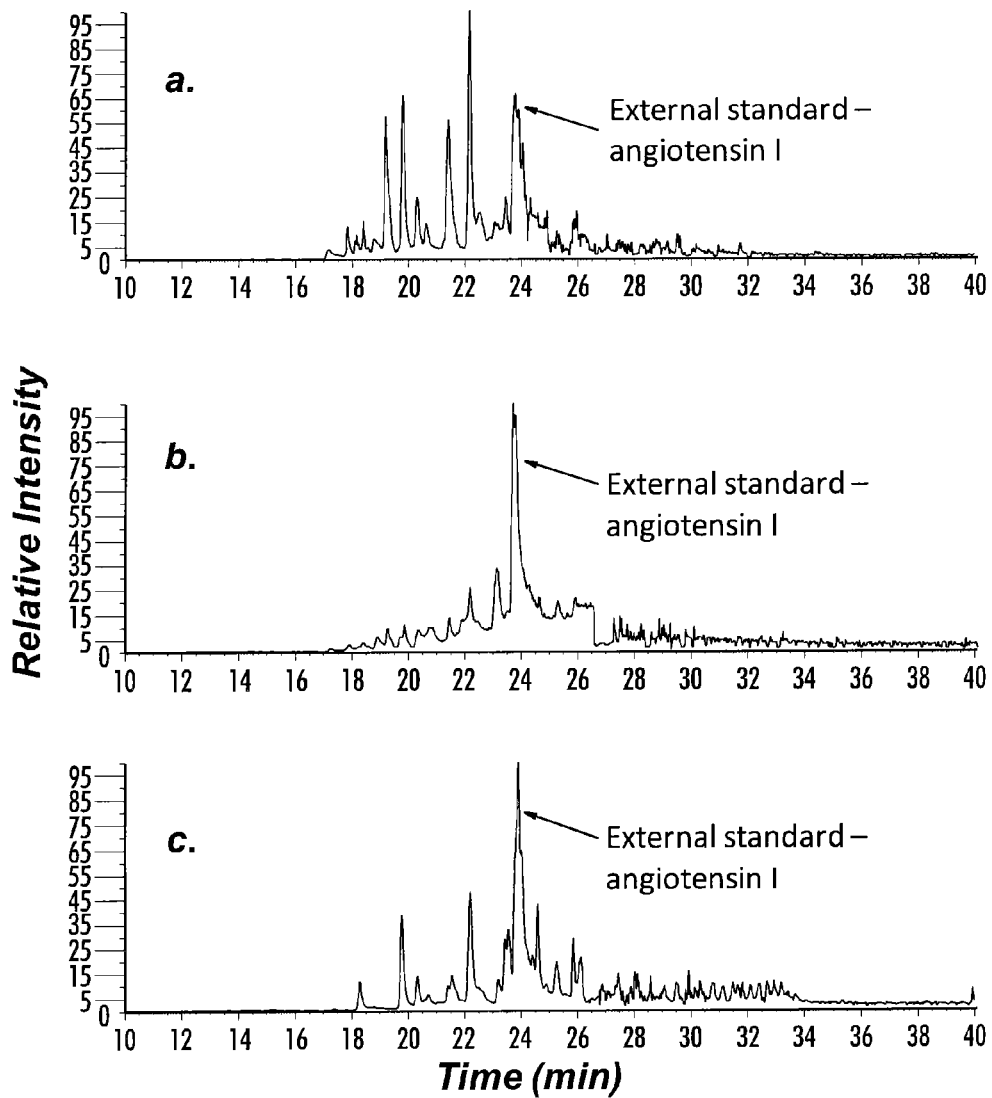
FIG. 14 is a chromatogram comparing dispersive pipette tip technology compared to fixed resin pipette tip technology according to an embodiment of the present invention.

As shown in FIG. 14, LC elution plots against MS intensities obtained from LTQ-Orbitrap Velos Pro of trypsin digested BSA de-salted and concentrated using dispersive micropipette tips (a. and c.) compared to fixed resin tips (b.). A stock of trypsin-digested BSA solution was aliquoted (3 pmol in 50 µL) and de-salted using dispersive technology (a.) and fixed resin (b.) then eluted with acetonitrile, followed by solvent evaporation and re-suspension in 10 µL of 2% acetonitrile in 0.1% formic acid/water containing same concentration of angiotensin I, an external standard. One µL of the solution was injected and analyzed. (c.) The stock trypsin-digested BSA solution was further diluted 10-fold (300 femptomol (fmol) in 50 µL), then de-salted/concentrated to 10 µL using dispersive micropipette tip and injected 1 µL for analysis. The results for (a.) and (c.) were taken after a dispersive pipette tip device 10 of the present invention was aspirated two times with a liquid sample. The results for (b.) were taken after a fixed resin reverse phase pipette tip was aspirated ten times with a liquid sample. Comparing (a.) and (c.) dispersive technology to (b.) fixed resin reverse phase pipette tips, the signals have higher signal to noise ratios and the results show more abundant peaks. This indicates that the dispersive technology in this example provides over a 10-fold improvement in sensitivity.

Those skilled in the chemical arts will appreciate from the foregoing description of preferred embodiments that substitutions and modification may be made without departing from the spirit and scope of the invention which is defined by the appended claims.

What is claimed is:

1. A pipette tip device for performing dispersive SPE, comprising:
   a pipette tip having an upper barrier and a lower barrier;
   sorbent material contained between said upper barrier and said lower barrier; and
   a baffle system contained and fixed within said pipette tip between said upper barrier and said lower barrier, wherein said baffle system is shaped to disrupt the movement of said sorbent material within said pipette tip when a liquid sample is introduced into said pipette tip.

2. The pipette tip device as recited in claim 1, wherein said lower barrier is a frit, a screen, a closure with a slit, or a closure with multiple slits.

3. The pipette tip device as recited in claim 1, wherein said baffle system is connected with said upper barrier.

4. The pipette tip device as recited in claim 1, wherein said upper barrier is a porous frit.

5. The pipette tip device as recited in claim 1, wherein said baffle system includes an insert that is above said sorbent material.

6. The pipette tip device as recited in claim 5, wherein said insert is a single, flat piece.

7. The pipette tip device as recited in claim 6, wherein said piece is rectangular in shape.

8. The pipette tip device as recited in claim 6, wherein said piece is round or oval.

9. The pipette tip device as recited in claim 6, wherein said piece is monolithic with the interior surface of said pipette tip.

10. The pipette tip device as recited in claim 1, wherein said baffle system includes an insert having an elongated cylindrical shape.

11. The pipette tip device as recited in claim 1, wherein said baffle system includes an insert having a central stem with one or more ribs extending out radially from the stem.

12. The pipette tip device as recited in claim 11, wherein said stem is formed by two intersecting ribs.

13. The pipette tip device as recited in claim 11, wherein said stem is formed by more than two intersecting ribs.

14. The pipette tip device as recited in claim 1, wherein said baffle system includes at least one ridge along the interior surface of said pipette tip.

15. The pipette tip device as recited in claim 1, wherein said baffle system includes four, evenly spaced ridges along the interior surface of said pipette tip.

16. The pipette tip device as recited in claim 14, wherein said at least one ridge is linear.

17. The pipette tip device as recited in claim 14, wherein said at least one ridge is spiral.

18. The pipette tip device as recited in claim 14, wherein said at least one ridge is annular.

19. The pipette tip device as recited in claim 1, wherein said baffle system is about parallel to the cylindrical axis of said pipette tip.

20. A pipette tip device for performing dispersive SPE, comprising:
    a pipette tip having a lower barrier and an upper barrier;
    sorbent material contained between said lower barrier and said upper barrier; and
    a baffle system that includes a fixed insert contained within said pipette tip and above said sorbent material and said lower barrier, wherein said baffle system is shaped to disrupt liquid flow when a liquid sample is aspirated into said pipette tip.

21. The pipette device as recited in claim 20, wherein said fixed insert is integral with the interior surface of said pipette tip.

22. A method for performing dispersive SPE, comprising the steps of:
    providing a pipette tip device, having an upper barrier and a lower barrier; sorbent material contained above said lower barrier; and a baffle system contained and fixed within said pipette tip between said upper barrier and said lower barrier;
    providing a sample solution;
    aspirating said sample solution into said pipette tip device; and
    mixing said sorbent material with said sample solution to perform an SPE extraction, wherein said baffle system is shaped to disrupt said sorbent material when in solution within said pipette tip.

23. The method as recited in claim 22, wherein said pipette tip has a volume of about 1 mL or less.

24. A method for performing dispersive SPE, comprising the steps of:
    providing a pipette tip device, having an upper barrier and a lower barrier; sorbent material contained above said lower barrier; and a baffle system including a fixed insert contained within said pipette tip between said upper barrier and said lower barrier;
    providing a sample solution;
    aspirating said sample solution into said pipette tip device;

mixing said sorbent material with said sample solutions to perform an SPE extraction, wherein said baffle system is shaped to disrupt said sorbent material when in solution;
dispensing the extracts from said SPE extraction to waste;
aspirating wash solvent into said pipette tip device;
mixing said sorbent material with said wash solvent;
dispensing said wash solvent to waste;
aspirating elution solvent into said pipette tip device;
mixing said sorbent with elution solvent; and
collecting the resulting eluate from said SPE extraction.

\* \* \* \* \*